United States Patent
Hewitt et al.

(10) Patent No.: US 9,023,893 B2
(45) Date of Patent: *May 5, 2015

(54) SYNERGISTIC COMBINATIONS COMPRISING A RENIN INHIBITOR FOR CARDIOVASCULAR DISEASES

(75) Inventors: William Hewitt, Pottstown, PA (US); Daniel L Vasella, Basel (CH); Randy L Webb, Flemington, NJ (US)

(73) Assignee: Novartis AG, Basel (CH)

( * ) Notice: Subject to any disclaimer, the term of this patent is extended or adjusted under 35 U.S.C. 154(b) by 108 days.

This patent is subject to a terminal disclaimer.

(21) Appl. No.: 13/235,659

(22) Filed: Sep. 19, 2011

(65) Prior Publication Data

US 2012/0004312 A1    Jan. 5, 2012

Related U.S. Application Data

(62) Division of application No. 10/416,039, filed as application No. PCT/EP01/13241 on Nov. 15, 2001, now Pat. No. 8,168,616.

(30) Foreign Application Priority Data

Nov. 17, 2000 (GB) .................................. 0028151.9

(51) Int. Cl.
| | |
|---|---|
| A61K 31/165 | (2006.01) |
| A61K 31/542 | (2006.01) |
| A61K 45/06 | (2006.01) |
| A61K 31/451 | (2006.01) |

(52) U.S. Cl.
CPC ............... *A61K 45/06* (2013.01); *A61K 31/542* (2013.01); *Y10S 514/869* (2013.01); *Y10S 514/929* (2013.01); *A61K 31/451* (2013.01); *A61K 31/165* (2013.01)

(58) Field of Classification Search
USPC ........................................................ 514/616
See application file for complete search history.

(56) References Cited

U.S. PATENT DOCUMENTS

| | | | |
|---|---|---|---|
| 4,782,043 | A | 11/1988 | Boger et al. |
| 4,812,442 | A | 3/1989 | Boger et al. |
| 5,164,388 | A | 11/1992 | De et al. |
| 5,182,266 | A | 1/1993 | Kleinert |
| 5,268,374 | A | 12/1993 | Fung et al. |
| 5,284,849 | A | 2/1994 | Rosenberg et al. |
| 5,308,846 | A | 5/1994 | Allen et al. |
| 5,559,111 | A | 9/1996 | Göschke et al. |
| 5,606,078 | A | 2/1997 | Göschke et al. |
| 5,627,182 | A | 5/1997 | Göschke et al. |
| 5,646,143 | A | 7/1997 | Göschke et al. |
| 5,654,445 | A | 8/1997 | Göschke et al. |
| 5,659,065 | A | 8/1997 | Göschke |
| 5,663,188 | A | 9/1997 | Fossa |
| 5,696,116 | A * | 12/1997 | Clozel et al. .................. 514/221 |
| 5,696,166 | A | 12/1997 | Yanni et al. |
| 5,705,658 | A | 1/1998 | Göschke et al. |
| 5,821,232 | A | 10/1998 | Fossa |
| 5,846,990 | A | 12/1998 | Murugesan et al. |
| 6,057,344 | A | 5/2000 | Young |
| 8,183,295 | B2 | 5/2012 | Feldman et al. |
| 2003/0114389 | A1 | 6/2003 | Webb |

FOREIGN PATENT DOCUMENTS

| | | |
|---|---|---|
| CA | 1279575 | 1/1991 |
| CA | 2128199 | 2/1997 |
| CA | 2259148 | 9/2009 |
| EP | 0311012 | 4/1989 |
| EP | 0498361 | 8/1992 |
| EP | 0678503 | 10/1992 |
| WO | WO 91/17771 | 11/1991 |
| WO | WO 92/00972 | 1/1992 |
| WO | WO 92/10097 | 6/1992 |
| WO | WO 96/22978 | 8/1996 |
| WO | WO 99/11260 | 3/1999 |
| WO | WO 99/65500 | 12/1999 |
| WO | WO 00/04862 | 2/2000 |
| WO | WO 01/34132 | 5/2001 |

OTHER PUBLICATIONS

Derwent Abstract, Amberg et al., WO00/37450, May 8, 2001, "New 3-acylamino-propionic acid and 3-sulfonylamino-propionic acid derivatives useful as endothelin receptor antagonists in treatment of derivatives useful as endothelin receptor antagonists in treatment of e.g. cardiovascular and renal disorders, migraine and cancer."
Webb et al., "Synergistic effects of combined converting enzyme inhibition and angiotensin II antagonism on blood pressure in conscious telemetered spontaneously hypertensive rats", Journal of Hypertension, vol. 16, no. 6, pp. 843-852, 1998.
Mutschler, E. et al., Arzneimittlewirkungen, Lehrbuch der Pharmakologie und Toxikologie, pp. 481-492, 1996.
Kleinert H., "Renin Inhibition", Cardiovascular Drugs and Therapy, No. 5, pp. 645-655, 1995.

(Continued)

*Primary Examiner* — Savitha Rao
*Assistant Examiner* — Gregg Polansky
(74) *Attorney, Agent, or Firm* — Jim Lynch

(57) ABSTRACT

The invention relates to a combination comprising the renin inhibitor of formula (I)

(I)

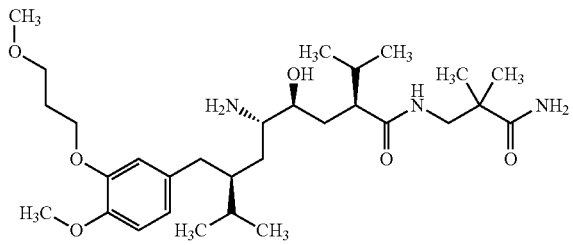

or a pharmaceutically acceptable salt thereof.

3 Claims, No Drawings

(56) References Cited

OTHER PUBLICATIONS

Himmelmann A. et al., Remikiren (RO 42-5892) An orally Active Renin Inhibitor in Essential Hypertension (Effects on Blood Pressure and the Renin-Angiotensin-Aldosterone System), American Journal of Hypertension, pp. 517-522, 1996.
Novartis Press Releases, "Novartis receives FDA approval for Valturna® a single-pill combination of valsartan and aliskiren, to treat high blood pressure", Sep. 17, 2009.
Frishman, "Comparison of Amlodipine and Benazepril Monotherapy to Amlodipine Plus Benazepril In Patients with Systemic Hypertension: A Randomized, Double-Blind, Placebo-Controlled, Parallel-Group Study", J Clin Pharmacol 1995; 35: 1060-1066.
Derwent Abstract, Amberg et al., WO00/37450, May 8, 2001, "New 3-acylamino-propionic acid and 3-sulfonylamino-propionic acid derivatives useful as endothelin receptor antagonists in treatment of derivatives useful as endothelin receptor antagonists in treatment of e.g. cardiovascular and renal disorders, migraine and cancer.".
Maqueda (Fixed-dose combination therapy: reduction of side effects with enhanced tolerance and antihypertensive efficacy, Rev Esp Cardiol (1999) 52:59-72, printed pp. 1.
Aliskiren (SPP-100, Ramilez) (O'Brien, E., Aliskiren: a renin inhibitor offering a new approach for the treatment of hypertension, Exdpert Opin. Investig. Drugs (2006) 15(10): 1269-1277, especially p. 1272.
National Public Health Partnership (2006). The Language of Prevention, printed pp. 1-9, especially pp. 5 and 9.
Steinfeldt et al., Therapeutic Combinations Comprising (poly adp-ribose) polymerases inhibitor, 2006, FreshPatents.com #20060074073, pp. 1-6.
Frank, J. in Managing hypertension using combination therapy Am Fam Physician May 1, 2008: 77(9): 1279-86, printed p. 1.
Weir, Matthew, "Antihypertensive Combination Therapy", Drugs of Today, vol. 34(1), pp. 5-9, 1998.
Jeremic et al., Effects of a new angiotensin-converting enzyme inhibitor (idrapril) in rats with left ventricular dysfunction after myocardial infarction, Journal of Cardiovascular Pharmacology, 27, pp. 347-354 (1996).
Oparil et al, "Efficacy and safety of combined use of aliskiren and valsartan in patients with hypertension: a randomised, double-blind trial", The Lancet, vol. 370, Jul. 21, 2007.
Webb et al., "Synergistic effects of combined converting enzyme inhibition and angiotensin II antagonism on blood pressure in conscious telemetered spontaneously hypertensive rats", Journal of Hypertension, vol. 16, No. 6, pp. 843-852, 1998.
Mutschler, E. et al., Arzneimittlewirkungen, Lehrbuch der Pharmakologie and Toxikologie, pp. 481-492, 1996.
Hypertension, vol. 36(4), pp. 693-698, 2000.
Kleinert H., "Renin Inhibition", Cardiovascular Drugs and Therapy, No. 5, pp. 645-55, 1995.
Weber, M.A. et al., "Assessment of renin dependency of hypertension with a dipeptide renin inhibitor", Circulation, vol. 81(6), pp. 1768-1774 1990.
Glassman H.N. et al., "Clinical Pharmacology of Enalkiren, a Novel, Dipeptide Renin Inhibitor", Journal of Cardiovascular Pharmacology, vol. 16, Suppl 4, pp. S76-S81, 1990.
Himmelmann A. et al., Remikiren (RO 42/5892) An orally Active Renin Inhibitor in Essential Hypertension (Effects on Blood Pressure and the Renin-Angiotensin-Aldosterone System), American Journal of Hypertension, pp. 517-522, 1996.
Menard J. et al., "Dose-Dependent Effects of the Renin Inhibitor Zankiren HCI After a Single Oral Dose in Mildly Sodium-Depleted Normotensive Subjects", Circulation, vol. 91, pp. 330-338, 1995.
U.S. Label Tekturna HCT, revised Jan. 2008.
Neutel J.M. et al., "Combination Therapy with Diuretics: An Evolution of Understanding", Am J. Med. vol. 101 (suppl. 3A, pp. 61S-70S, 1996.
Clinical Research, vol. 37, No. 2, 1989.
Friday Evening Poster Session, Clinical Research, vol. 48, No. 2, 1990.
Novartis Press Releases, "Novartis receives FDA approval for Valtuma® a single-pill combination of valsartan and aliskiren, to treat high blood pressure", Sep. 17, 2009.
Rahuel J et al., "Structure-based drug design: the discovery of novel nonpeptide orally active inhibitors of human renin", Chemistry & Biology, vol. 7, pp. 493-504, Jul. 2000.
Clozel et al., "Comparative effects of three different potent rennin inhibitors in primates" Hypertension, vol. 22, pp. 9-17, 1993.
Rabassed X, et al, "Antihypertensive treatment of heart failure aldosterone antagonist", vol. 25, No. 5, pp. 488-501, XP009013107, Jan. 2000, Drugs of the Future, 1999.
Scatena, R., "Bosentan Roche". Current Opinion in Cardiovascular Pulmonary and Renalinvestigational Drugs, (London, GB) vol. 1, No. 3, pp. 375-396, XP008097711, Jan. 1999.
Lefevre, et al., Automated quantitative determiniation of the new renin inhibitor CGP 60536 by high-performance liquid chromatography, Journal of Chromatography B. vol. 738, pp. 129-136, 2000.
Rahuel, et al., Structure-based drug design: the discovery of novel non-peptide orally active inhibitors of human renin, vol. 7, pp. 493-504, 2000, Chemistry & Biology.
Calhoun, D et al., Poster Conference of the International Society of Hypertension, May 16-20, 2006, New York.
Lijnen, P et al., Effect of Chronic Diuretic Treatment on the Plasma Renin-Angiotensin-Aldosterone System in Essential Hypertension, Br. J. Clin. Pharmac., vol. 12, pp. 387-392, 1981.
Van Der Vring et al., "T-Channel-Selective Calcium Channel Blockade: A Review of Published Data and Therapeutic Potential", Current Therapeutic Research, Vol. 59, No. 11, Nov. 1998, pp. 754-761.
Schumacher et al., 2008, Speedel, Aldosterone Synthase Inhibitors, 17 pages.
Hong Lu et al., 2008, "Renin inhibition reduces hypercholesterolemia-induced atherosclerosis in mice", J. Clin. Investigation, 118(3):984-993.
Wood et al., 2005, "Aliskiren, a novel, orally effective renin inhibitor, lowers blood pressure in marmosets and spontaneously hypertensive rats", Journal of Hypertension, 23:417-426.
Munger, et al. "Aliskiren as add-on to amlodipine provides significant additional blood pressure lowering without increased oedema associated with doubling the amlodipine dose", Eur Heart J. 2006;25(suppl): 117. Abstract: P784.
Drummond et al., 2007, "Antihypertensive efficacy of the oral direct renin inhibitor aliskiren as add-on therapy in patients not responding to amlodipine monotherapy", Journal of Clinical Hypertension, 9(10):742-750.

* cited by examiner

SYNERGISTIC COMBINATIONS COMPRISING A RENIN INHIBITOR FOR CARDIOVASCULAR DISEASES

This is a divisional of application Ser. No. 10/416,039 filed on Jul. 25, 2003, which is a National Stage of International Application No. PCT/EP01/13241 filed on Nov. 15, 2000, the entire disclosures of which are hereby incorporated by reference.

The invention relates to a combination, such as a combined preparation or pharmaceutical composition, respectively, comprising the renin inhibitor of formula (I)

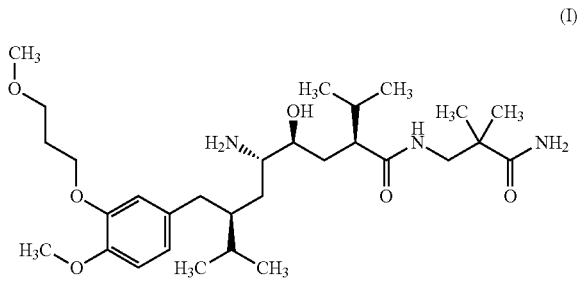 [SMILES: COCCCOc1cc(C[C@@H](C[C@H](N)[C@@H](O)C[C@H](C(=O)NCC(C)(C)C(N)=O)C(C)C)C(C)C)ccc1OC]

(I)

or a pharmaceutically acceptable salt thereof.

The invention especially relates to a combination, such as a combined preparation or pharmaceutical composition, respectively, comprising the renin inhibitor of formula (I) or a pharmaceutically acceptable salt thereof and at least one therapeutic agent selected from the group consisting of (i) an $AT_1$-receptor antagonist or a pharmaceutically acceptable salt thereof,
(ii) a HMG-Co-A reductase inhibitor or a pharmaceutically acceptable salt thereof,
(iii) an angiotensin converting enzyme (ACE) inhibitor or a pharmaceutically acceptable salt thereof,
(iv) an Calcium channel blocker or a pharmaceutically acceptable salt thereof,
(v) an aldosterone synthase inhibitor or a pharmaceutically acceptable salt thereof,
(vi) an aldosterone antagonist or a pharmaceutically acceptable salt thereof,
(vii) an dual angiotensin converting enzyme/neutral endopetidase (ACE/NEP) inhibitor or a pharmaceutically acceptable salt thereof,
(viii) an endothelin antagonist or a pharmaceutically acceptable salt thereof, and
(ix) a diuretic or a pharmaceutically acceptable salt thereof.

The term "at least one therapeutic agent" shall mean that in addition to the compound of formula (I) one or more, for example two, furthermore three, active ingredients as specified according to the present invention can be combined.

Renin inhibit the action of the natural enzyme renin. The latter passes from the kidneys into the blood where it effects the cleavage of angiotensinogen, releasing the decapeptide angiotensin I which is then cleaved in the lungs, the kidneys and other organs to form the octapeptide angiotensinogen II. The octapeptide increases blood pressure both directly by arterial vasoconstriction and indirectly by liberating from the adrenal glands the sodium-ion—retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of e.g. the hypotensive effect of renin inhibitors.

The renin inhibitor of formula (I), chemically defined as 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide, is specifically disclosed in EP 678503A. Especially preferred is the hemi-fumarate salt thereof.

$AT_1$-receptor antagonists (also called angiotensin II receptor antagonists) are understood to be those active ingredients that bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds that are selected from the group consisting of valsartan (cf. EP 443983), losartan (cf. EP253310), candesartan (cf. 459136), eprosartan (cf. EP 403159), irbesartan (cf. EP454511), olmesartan (cf. EP 503785), tasosartan (cf. EP539086), telmisartan (cf. EP 522314), the compound with the designation E-1477 of the following formula

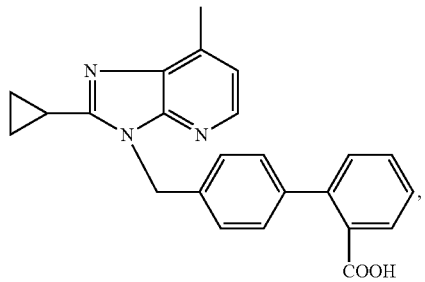 [SMILES: Cc1ccnc2c1nc(C1CC1)n2Cc1ccc(-c2ccccc2C(=O)O)cc1]

the compound with the designation SC-52458 of the following formula

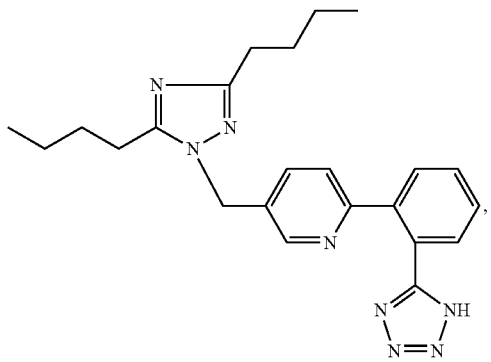 [SMILES: CCCCc1nc(CCCC)n(Cc2ccc(-c3ccccc3-c3nnn[nH]3)nc2)n1]

and the compound with the designation the compound ZD-8731 of the following formula

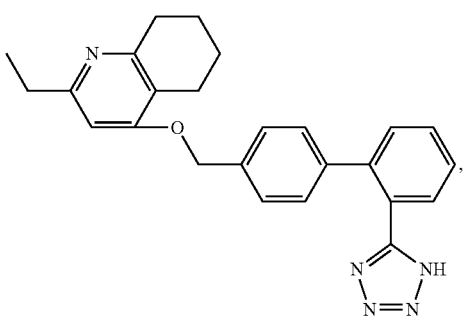 [SMILES: CCc1cc(OCc2ccc(-c3ccccc3-c3nnn[nH]3)cc2)c2c(n1)CCCC2]

or, in each case, a pharmaceutically acceptable salt thereof.

Preferred AT$_1$-receptor antagonist are those agents that have been marketed, most preferred is valsartan or a pharmaceutically acceptable salt thereof. HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin and also atorvastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibef radii, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs. Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

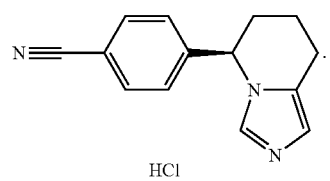 [SMILES: N#Cc1ccc([C@H]2CCCc3cncn32)cc1 ; Cl]

A preferred steroidal aldosterone antagonist is eplerenone (cf. EP 122232 A) of the formula

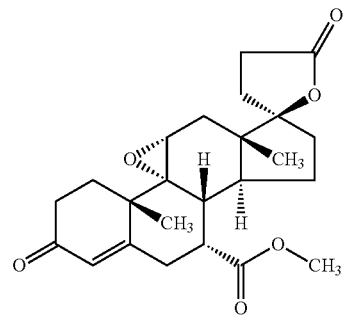

or
spironolactone.

Compounds having an inhibitory effects on both angiotensin converting enzyme and neutral endopetidase, so-called dual ACE/NEP inhibitors, can be used for the treatment of cardiovascular pathologies.

A preferred dual angiotensin converting enzyme/neutral endopetidase (ACE/NEP) inhibitor is, for example, omapatrilate (cf. EP 629627), fasidotril or fasidotrilate, or Z 13752A (cf. WO 97/24342) or, if appropriable, a pharmaceutically acceptable salt thereof.

Endothelin (ET) is a highly potent vasoconstrictor peptided synthesized and released by the vascular endotleium. Endothelin exists in three isoforms (ET-1, ET-2 and ET-3). (ET shall meand any or all other isoforms of ET). Elevated levels of ET have been reported in plasma fomr patients with e.g. essential hypertension. Endothelin receptor antagonist can be used to inhibit the vasoconstrictive effects induced by ET.

A preferred endothelin antagonist is, for example, bosentan (cf. EP 526708 A), enrasentan (cf. WO 94/25013), atrasentan (cf. WO 96/06095), especially atrasentan hydrochloride, darusentan (cf. EP 785926 A), BMS 193884 (cf. EP 702012 A), sitaxentan (cf. U.S. Pat. No. 5594021), especially sitaxsentan sodium, YM 598 (cf. EP 882719 A), S 0139 (cf. WO 97/27314), J 104132 (cf. EP 714897 A or WO 97/37665), furthermore, tezosentan (cf. WO 96/19459), or in each case, a pharmaceutically acceptable salt thereof.

A diuretic is, for example, a thiazide derivative selected from the group consisting of chlorothiazide, hydrochlorothiazide, methylciothiazide, and chlorothalidon. The most preferred is hydrochlorothiazide.

Preferred are combinations, such as a combined preparations or pharmaceutical compositions, respectively, comprising the renin inhibitor of formula (I) or a pharmaceutically accepted salt thereof and as second active agent an active agent selected from the group consisting of valsartan, fluvastatin, atorvastatin, pitavastatin, benzepril, enalapril, amlodipine, especially the besylate thereof, the (+) enantiomer of fadrozole, eplerenone, omapatrilate, Z 13752A, sitaxsentan, especially sitaxsentan sodium, darusentan and hydrochlorothiazide.

Furthermore preferred are combinations, such as a combined preparations or pharmaceutical compositions, respectively, comprising the renin inhibitor of formula (I) or a pharmaceutically accepted salt thereof and one active agent selected from the group consisting of valsartan, fluvastatin, atorvastatin, pitavastatin, benzepril, enalapril, amlodipine, especially the besylate thereof, the (+) enantiomer of fadrozole, eplerenone, omapatrilate, Z 13752A, sitaxsentan, especially sitaxsentan sodium, and darusentan, furthermore comprising as third active agent hydrochlorothiazide.

The structure of the active agents identified by generic or tradenames may be taken from the actual edition of the standard compendium "The Merck index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or a pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

All the more surprising is the experimental finding that the combined administration of the renin inhibitor of formula (I) or a salt thereof with a therapeutic agent selected from the group consisting of (i) to (ix) results not only in a beneficial, especially a synergistic, therapeutic effect, but also in additional benefits resulting from the combined treatment and further surprising beneficial effects compared to a monotherapy applying only one of the pharmaceutically active compounds used in the combinations disclosed herein.

In particular, all the more surprising is the experimental finding that the combination of the present invention results not only in a beneficial, especially a synergistic, therapeutic effect but also in additional benefits resulting from combined treatment such as a surprising prolongation of efficacy, a broader variety of therapeutic treatment and surprising beneficial effects on diseases and conditions as specified hereinafter.

It can be shown by established test models and especially those test models described herein that the combination of the renin inhibitor of formula (I) with a therapeutic agent selected from the group consisting of (i) to (ix) results in a more effective prevention or preferably treatment of diseases specified in the following. In particular, it can be shown by established test models and especially those test models described herein that the combination of the present invention results in a more effective prevention or preferably treatment of diseases specified hereinafter.

If taken simultaneously, this results not only in a further enhanced beneficial, especially a synergistic, therapeutic effect, but also in additional benefits resulting from the simultaneous treatment such as a surprising prolongation of efficacy, a broader variety of therapeutic treatment and surprising beneficial effects, e.g. less increase of weight, on diseases and conditions associated with diabetes mellitus, for a number of combinations as described herein. Moreover, for a human patient, especially for elderly people, it is more convenient and easier to remember to take two tablets at the same time, e.g. before a meal, than staggered in time, i.e. according to a more complicated treatment schedule. More preferably, both active ingredients are administered as a fixed combination, i.e. as a single tablet, in all cases described herein. Taking a single tablet is even easier to handle than taking two tablets at the same time. Furthermore, the packaging can be accomplished with less effort.

The term "synergistic" as used herein means that the effect achieved with the methods and compositions of the present invention is greater than the sum of the effects that result from methods and compositions comprising the active ingredients of this invention separately.

The person skilled in the pertinent art is fully enabled to select a relevant and standart animal test model to prove the hereinbefore and hereinafter indicated therapeutic indications and beneficial effects.

The pharmaceutical activities as effected by administration of representatives of the class of $AT_1$-receptor antagonists or ACE inhibitors, respectively, or of the combination of active agents used according to the present invention can be demonstrated e.g. by using corresponding pharmacological models known in the pertinent art. The person skilled in the pertinent art is fully enabled to select a relevant animal test model to prove the hereinbefore and hereinafter indicated therapeutic indications and beneficial effects.

The beneficial effects on blood pressure can, for example, be demonstrated in the test model as disclosed in R. L. Webb et al., in J. Hypertension, 16:843-852, 1998.

Methods:

The combination according to the present invention comprising the compound of formula (I) or a pharmaceutically acceptable salt thereof can be administered by various routes of administration but are tested in this example using a continuous infusion via subcutaneously-implanted osmotic minipumps. Each agent can be tested over a wide-range of dosages to determine the optimal drug level for each agent in combination to elicit the maximal response. For these studies, it is preferred to use treatment groups consisting of at least 6 animals per group. Each study is best performed in which the effects of the combination treatment group are determined at the same time as the individual components are evaluated. Although drug effects may be observed with acute administration (such as 1 day), it is preferable to observe responses in a chronic setting as shown below in which experiments were done over a two to three week observation period. The long-term study is of sufficient duration to allow for the full development of compensatory responses to occur and therefore, the observed effect will most likely depict the actual responses of the test system representing sustained or persistent effects. The effects on blood pressure depicted below represent a synergistic antihypertensive effect when the two agents are used in combination.

Statistical Analysis:

The combination therapy can be compared to that of the monotherapy groups by determining the maximum change in blood pressure or the area under the curve (AUC) for change in blood pressure over time in each of the treatment groups. All values are represented as the group mean±SEM. Statistical significance is obtained when $p<0.05$. The AUC values for each of the treatment groups can be compared statistically using a one-way ANOVA followed by the appropriate post-hoc analysis, for example by performing a Tukey's test.

Results:

Blood pressure can be reduced to a similar degree using lower dosages of each of the components when given in combination than when the individual monotherapies are administered. An additional unexpected finding is that the blood pressure can be lowered to a greater extent with the combination than when the individual compound of formula (I) or a pharmaceutically acceptable salt thereof is given alone at a higher dosage.

These beneficial effects can, for example, be demonstrated in the test model as disclosed by G. Jeremic et al. in J. Cardovasc. Pharmacol. 27:347-354, 1996.

For example, the valuable potential of the combination of the present invention for the prevention and treatment of myocardial infarction (including the post-myocardial infarction indication to delay the progression to congestive heart failure) can be found using the following test model.

Study Design

In the study to be performed, permanent coronary artery occlusion (CAO) in rats is used as a model of acute myocardial infarction. The experiments are carried out with 5 treatment groups characterized by following features:
  sham-operated animals
  CAO+vehicle
  CAO+compound of formula (I) or a pharmaceutically accetable salt, especially the hemi-fumarate, thereof,
  CAO+aldosterone synthase inhibitor
  CAO+compound of formula (I) or a pharmaceutically accetable salt, especially the hemi-fumarate, thereof, +aldosterone synthase inhibitor.

Following doses and routes of administration can be applied:

For the (+)-enantioner of the hydrochloride of fadrozole Alza osmotic minipumps 0.4 mg/kg/d.
  During the study following variables are measured:
  infarct size
  LV chamber volume
  interstitial and perivascular collagen density in spared LV myocardium
  COL-I and COL-III protein content in spared LV myocardium by Western blot
  cardiomyocytes cross-sectional area and length in sections of LV myocardium
  plasma concentrations of renin and aldosterone
  urine concentration of sodium, potassium and aldosterone
  blood pressure in conscious animals
  LV and carotid blood pressure in anesthetized animals.

Methodology

Infarct size: Six μm-thick transverse histological sections of the left ventricle are stained with nitroblue tetrazolium and acquired by a B/W XC-77CE CCD video camera (Sony). The resulting image is processed on a KS 300 image analysis system (Carl Zeiss Vision) using a software specifically developed (Porzio at al., 1995). A single operator blinded to treatment interactively defines the boundaries of the interventricular septum, and the infarcted area on each section is semiautomatically identified as the area of unstained ventricular tissue. The software automatically calculates for each component of the ventricular section defined as the chamber, septum, infarcted area, infarcted LV wall and viable LV wall, a set of geometric parameters (Porzio et al., 1995).

Histology: Hearts are fixed in situ, by retrograde perfusion with buffered 4% formaldehyde after arrest in diastole by i.v. injection of 0.5 M KCl. After fixation, the left ventricle (LV) and the free wall of the right ventricle are separately weighed; LV longer diameter is measured with a caliper. LV histological sections are stained with hematoxylin & eosin for qualitative examination and to quantify cardiomyocytes cross-sectional area with a semi-automated image analysis routine. Interstitial collagen deposition in LV is evaluated on Sirius red stained sections with a semi-automated image analysis routine (Masson et al., 1998).

Collagen content in LV spared myocardium: LV tissue in the spared myocardium is homogenized, subjected to PAGE-SDS electrophoresis and electroblotted onto nitrocellulose membrane. The blots are exposed to primary antibodies, i.e. rabbit anti-rat collagen type I or type III antiserum (Chemicon). The primary antibodies are recognized by secondary antibodies conjugated to alkaline phosphatase (for colagen type I) or peroxidase (collagen type III).

Left ventricular chamber volume: LV chamber volume is determined in hearts arrested in diastole (KCl) and fixed in formalin under a hydrostatic pressure equivalent to the measured LV end-diastolic pressure. A metric rod is inserted into the LV to measure LV inner length. The transverse diameters of the LV chamber are measured in two 1-mm thick transverse sections near to the base and the apex of the ventricle (Jeremic et al., 1996). The chamber volume is computed from an equation integrating transverse diameters and inner length.

Systemic and Left ventricular hemodynamics: A microtip pressure transducer (Millar SPC-320) connected to a recorder (Windograf, Gould Electronics) is inserted into the right carotid artery to record systolic and diastolic blood pressures. The pressure transducer is advanced into the LV to measure LV systolic (LVSP) and end-diastolic (LVEDP) pressures, the first derivative of LV pressure over time (+dP/dt) and heart rate.

Non-invasive blood pressure: Systolic blood pressure and heart rate are measured by the tail-cuff method (Letica LE 5002) in conscious rats.

Urine electrolytes, hormones: Rats are individually housed in metabolic cages and 24-h urine collected on 1 ml HCl 6N. Water intake is measured. Urine catecholamines are extracted on Bondelut $C_{18}$ columns (Varian), separated by HPLC (Apex-II C18, 3 μm, 50×4.5 mm analytical column, Jones Chromatography) and quantified with an electrochemical detector (Coulochem II, ESA) (Goldstein et al., 1981). Plasma and urine aldosterone, and plasma angiotensin II are determined with specific radioimmunoassays (Aldoctk-2, DiaSorin and Angiotensin II, Nichols Diagnostics). Urine sodium and potassium are measured by flame photometry.

Sample Size 10 animals analyzable in each treatment groups are sufficient to detect biologically significant differences. Only rats with an infarct size of at least 10% of the LV section area are included in the final analysis.

Endothelial dysfunction is being acknowledged as a critical factor in vascular diseases. The endothelium plays a bimodal role as the source of various hormones or by-products with opposing effects: vasodilation and vasoconstriction, inhibition or promotion of growth, fibrinolysis or thrombogenesis, production of anti-oxidants or oxidising agents.

Genetically predisposed hypertensive animals with endothelial dysfunction constitute a valid model for assessing the efficacy of a cardiovascular therapy.

Endothelial disfunction is characterized by, for example, increased oxidative stress, causing decreased nitric oxide, increased factors involved in coagulation or fibrinolysis such as plasminogen activating inhibitor-1 (PAI-1), tissue factor (TF), tissue plasminogen activator (tPA), increased adhesion molecules such as ICAM and VCAM, increased growth factors such as bFGF, TGFb, PDGF, VEGF, all factors causing cell growth inflammation and fibrosis.

The treatment e.g. of endothelial dysfunction can be demonstrated in the following pharmacological test:

Material and Methods

Male 20-24 week-old SHR, purchased from RCC Ldt (Fullingsdorf, Switzerland), are maintained in a temperature- and light-controlled room with free access to rat chow (Nafag 9331, Gossau, Switzerland) and tap water. The experiment is performed in accordance with the NIH guidelines and approved by the Canton Veterinary office (Bew 161, Kantonales Veterinäramt, Liestal, Switzerland). All rats are treated with the NO synthesis inhibitor L-NAME (Sigma Chemicals) administered in drinking water (50 mg/l) for 12 weeks. The average daily dose of L-NAME calculated from the water consumed was 2.5 mg/kg/d (range 2.1-2.7).

The rats can be divided into 5 groups: group 1, control (n=40); Group 2, the compound of formula (I) in form of the hemi-fumarate (ren1; n=40); Group 3, enalapril (ena1; n=30); Group 4, a combination (ena1ren1) of enalapril and the compound of formula (I) in form of the hemi-fumarate; (n=30) and Group 5, the compound of formula (I) in form of the hemi-fumarate (ren2–higher dose; n=30). The drugs are administered in drinking fluid. The dose of enalapril is selected from the work of Sweet et al. (1987) indicating significantly increased survival in rats with healed myocardial infarction. The pressor effect of Ang II at 1 mg/kg obtained in controls normotensive rats can be reduced after treatment with the compound of formula (I) in form of the hemi-fumarate (Gervais et al. 1999).

Body weight is measured every week. Systolic blood pressure and heart rate are recorded by tail cuff plethysmography 3 and 2 weeks before starting the study and at 2 weeks after drug administration. Urine is collected over a 24 hour period from rats kept in individual (metabolic) cages the week before starting treatment and at weeks 4 and 12 for volume measurement and protein, creatinine, sodium and potassium determination using standard laboratory methods. At the same time points, blood samples are withdrawn from the retro-orbital plexus (maximum 1 ml) for creatinine, Na and $K^+$ assays.

Ten rats from each group are sacrificed at 4 weeks for collection of kidney and heart for morphological analysis. The remaining rats are sacrificed at 12 weeks. Cardiac and kidney weight is recorded. Terminal blood sampling is performed in 5% EDTA at 4 (morphometry study) and 12 (end of the study) weeks for aldosterone, determination by radioimmunoassay using a DPC coat-a-count aldosterone-RIA kit (Bühlmann, Switzerland).

Statistical Analysis:

All data are expressed as mean±SEM. Statistical analysis is performed using a one-way ANOVA, followed by a Duncan's multiple range test and a Newman-Keuls test, 7 for comparison between the different groups. Results with a probability value of less than 0.05 are deemed statistically significant.

Results:

Even at non-blood pressure reducing doses, both the compound of formula (I) in form of the hemi-fumarate and enalapril treatment lead to significant improvements in survival rates.

The surprising observation is that, in this model, blockade of the RAS with low doses of the renin inhibitor of formula (I) and, for example, and enalapril improved survival despite persistent kidney dysfunction and high blood pressure. There is no decrease in proteinuria and no reduction of kidney lesions. Kidney and heart sections show glomerulosclerosis, fibrinoid necrosis and fibrosis. These results clearly demonstrate that survival of SHR with endothelial dysfunction is independent of the blood-pressure lowering effect of the treatment and may be related to a direct effect on the endothelium.

An improvement of regression of artherosclerosis without effecting the serum lipid levels can, for example, be demonstrated by using the animal model as disclosed by H. Kano et al. in Biochemical and Biophysical Research Communications 259, 414-419 (1999).

That the compounds or combinations according to the present invention can be used for the regression of a cholesterol diet-induced atherosclerosis, can be demonstrated using the test model described, e.g., by C. Jiang et al. In Br. J. Pharmacol. (1991), 104, 1033-1037.

That the compounds or combinations according to the present invention can be used for the treatment of renal failure, especially chronic renal failure, can be demonstrated using the test model described, e.g., by D. Cohen et al. in Journal of Cardiovascular Pharmacology, 32: 87-95 (1998).

Further benefits when applying the composition of the present invention are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

Preferably, the jointly therapeutically effective amounts of the active agents according to the combination of the present invention can be administered simultaneously or sequentially in any order, separately or in a fixed combination.

The pharmaceutical composition according to the present invention as described hereinbefore and hereinafter may be used for simultaneous use or sequential use in any order, for separate use or as a fixed combination.

Accordingly, the invention furthermore relates to a method for the prevention of, delay of progression of, treatment of a disease or condition selected from the group consisting of
(a) hypertension, congestive heart failure, renal failure, especially chronic renal failure, restenosis after percutaneous transluminal angioplasty, and restenosis after coronary artery bypass surgery;
(b) atherosclerosis, insulin resistance and syndrome X, diabetes mellitus type 2, obesity, nephropathy, renal failure, e.g. chronic renal failure, hypothyroidism, survival post myocardial infarction (MI), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;
(c) endothelial dysfunction with or without hypertension,
(d) hyperlipidemia, hyperlipoproteinemia, atherosclerosis and hypercholesterolemia, (e) glaucoma; furthermore
(f) isolated systolic hypertension (ISH), (g) diabetic retinopathy, and
(h) peripheral vascular disease; comprising administering to a warm-blooded animal, including man, in need thereof a jointly effective amount of a combination of the renin inhibitor of formula (I) or a pharmaceutically acceptable salt thereof with at least one therapeutic agent selected from the group consisting of
(i) an $AT_1$-receptor antagonist or a pharmaceutically acceptable salt thereof,
(ii) a HMG-Co-A reductase inhibitor or a pharmaceutically acceptable salt thereof,
(iii) an angiotensin converting enzyme (ACE) inhibitor or a pharmaceutically acceptable salt thereof,
(iv) an Calcium channel blocker or a pharmaceutically acceptable salt thereof,
(v) an aldosterone synthase inhibitor or a pharmaceutically acceptable salt thereof,
(vi) an aldosterone antagonist or a pharmaceutically acceptable salt thereof,
(vii) an dual angiotensin converting enzyme/neutral endopetidase (ACE/NEP) inhibitor or a pharmaceutically acceptable salt thereof,
(viii) an endothelin antagonist or a pharmaceutically acceptable salt thereof, and
(ix) a diuretic or a pharmaceutically acceptable salt thereof.

Furthermore, the present invention relates to the use of a combination of the renin inhibitor of formula (I) or a pharmaceutically acceptable salt thereof with at least one therapeutic agent selected from the group consisting of
(i) an $AT_1$-receptor antagonist or a pharmaceutically acceptable salt thereof,
(ii) a HMG-Co-A reductase inhibitor or a pharmaceutically acceptable salt thereof,
(iii) an angiotensin converting enzyme (ACE) inhibitor or a pharmaceutically acceptable salt thereof,
(iv) an Calcium channel blocker or a pharmaceutically acceptable salt thereof,
(v) an aldosterone synthase inhibitor or a pharmaceutically acceptable salt thereof,
(vi) an aldosterone antagonist or a pharmaceutically acceptable salt thereof,
(vii) an dual angiotensin converting enzyme/neutral endopetidase (ACE/NEP) inhibitor or a pharmaceutically acceptable salt thereof, and
(viii) an endothelin antagonist or a pharmaceutically acceptable salt thereof, and
(ix) a diuretic or a pharmaceutically acceptable salt thereof; for the manufacture of a medicament for the prevention of, delay of progression of, or treatment of a disease or condition selected from the group consisting of
(a) hypertension, congestive heart failure, renal failure, especially chronic renal failure, restenosis after percutaneous transluminal angioplasty, and restenosis after coronary artery bypass surgery;
(b) atherosclerosis, insulin resistance and syndrome X, diabetes mellitus type 2, obesity, nephropathy, renal failure, e.g. chronic renal failure, hypothyroidism, survival post myocardial infarction (MI), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;
(c) endothelial dysfunction with or without hypertension, comprising administering the pharmaceutical composition of the present invention;
(d) hyperlipidemia, hyperlipoproteinemia, atherosclerosis and hypercholesterolemia;
(e) glaucoma; furthermore
(f) isolated systolic hypertension (ISH),
(g) diabetic retinopathy, and
(h) peripheral vascular disease.

The invention furthermore relates to a pharmaceutical composition for the prevention of, delay of progression of, treatment of a disease or condition selected from the group consisting of
(a) hypertension, congestive heart failure, renal failure, especially chronic renal failure, restenosis after percutaneous transluminal angioplasty, and restenosis after coronary artery bypass surgery;
(b) atherosclerosis, insulin resistance and syndrome X, diabetes mellitus type 2, obesity, nephropathy, renal failure, e.g. chronic renal failure, hypothyroidism, survival post myocardial infarction (MI), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;
(c) endothelial dysfunction with or without hypertension, comprising administering the pharmaceutical composition of the present invention;
(d) hyperlipidemia, hyperlipoproteinemia, atherosclerosis and hypercholesterolemia;
(e) glaucoma; furthermore
(f) isolated systolic hypertension (ISH),
(g) diabetic retinopathy, and
(h) peripheral vascular disease; comprising a combination of the renin inhibitor of formula (I) or a pharmaceutically acceptable salt thereof with at least one therapeutic agent selected from the group consisting of
(i) an $AT_1$-receptor antagonist or a pharmaceutically acceptable salt thereof,
(ii) a HMG-Co-A reductase inhibitor or a pharmaceutically acceptable salt thereof,
(iii) an angiotensin converting enzyme (ACE) inhibitor or a pharmaceutically acceptable salt thereof,
(iv) an Calcium channel blocker or a pharmaceutically acceptable salt thereof,
(v) an aldosterone synthase inhibitor or a pharmaceutically acceptable salt thereof,
(vi) an aldosterone antagonist or a pharmaceutically acceptable salt thereof,
(vii) an dual angiotensin converting enzyme/neutral endopetidase (ACE/NEP) inhibitor or a pharmaceutically acceptable salt thereof,
(viii) an endothelin antagonist or a pharmaceutically acceptable salt thereof, and
(ix) a diuretic or a pharmaceutically acceptable salt thereof; and a pharmaceutically acceptable carrier.

Further benefits when applying the composition of the present invention are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

Preferably, the jointly therapeutically effective amounts of the active agents according to the combination of the present invention can be administered simultaneously or sequentially in any order, separately or in a fixed combination.

The pharmaceutical composition according to the present invention as described hereinbefore and hereinafter may be used for simultaneous use or sequential use in any order, for separate use or as a fixed combination.

A further aspect of the present invention is a kit for the prevention of, delay of progression of, treatment of a disease or condition according to the present invention comprising
(a) an amount of the renin inhibitor of formula (I) or a pharmaceutically accetable salt thereof in a first unit dosage form;
(b) an amount of at least one therapeutic agent selected from the group consisting of components (i) to (ix), or, in each case, where appropriate, a pharmaceutically acceptable salt thereof in a second etc. unit dosage form; and
(c) a container for containing said first, second etc. unit forms.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The invention furthermore relates to a commercial package comprising the combination according to the present invention together with instructions for simultaneous, separate or sequential use.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubilizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those which are commerically available.

Normally, in the case of oral administration, an approximate daily dose of from about 1 mg to about 360 mg is to be estimated e.g. for a patient of approximately 75 kg in weight.

The dosage of the active compound can depend on a variety of factors, such as mode of administration, homeothermic species, age and/or individual condition.

The pharmaceutical preparation will be supplied in the form of suitable dosage unit form, for example, a capsule or tablet, and comprising an amount, being together with the further component(s) jointly effective, e.g.

The doses of renin inhibitor of formula (I) to be administered to warm-blooded animals, for example human beings, of, for example, approximately 70 kg body weight, especially the doses effective in the inhibition of the enzyme renin, e.g. in lowering blood pressure and/or in improving the symptoms of glaucoma, are from approximately 3 mg to approximately 3 g, preferably from approximately 10 mg to approximately 1 g, for example approximately from 20 mg to 200 mg, per person per day, divided preferably into 1 to 4 single doses which may, for example, be of the same size. Usually, children receive about half of the adult dose. The dose necessary for each individual can be monitored, for example by measuring the serum concentration of the active ingredient, and adjusted to an optimum level. Single doses comprise, for example, 10, 40 or 100 mg per adult patient.

Valsartan, as a representative of the class of $AT_1$-receptor antagonists, will be supplied in the form of suitable dosage unit form, for example, a capsule or tablet, and comprising a therapeutically effective amount, e.g. from about 20 to about 320 mg, of valsartan which may be applied to patients. The application of the active ingredient may occur up to three times a day, starting e.g. with a daily dose of 20 mg or 40 mg of valsartan, increasing via 80 mg daily and further to 160 mg daily up to 320 mg daily. Preferably, valsartan is applied twice a day with a dose of 80 mg or 160 mg, respectively, each. Corresponding doses may be taken, for example, in the morning, at mid-day or in the evening. Preferred is b.i.d. administration.

In case of HMG-Co-A reductase inhibitors, preferred dosage unit forms of HMG-Co-A reductase inhibitors are, for example, tablets or capsules comprising e.g. from about 5 mg to about 120 mg, preferably, when using fluvastatin, for example, 20 mg, 40 mg or 80 mg (equivalent to the free acid) of fluvastatin, for example, administered once a day.

In case of ACE inhibitors, preferred dosage unit forms of ACE inhibitors are, for example, tablets or capsules comprising e.g. from about 5 mg to about 20 mg, preferably 5 mg, 10 mg, 20 mg or 40 mg, of benazepril; from about 6.5 mg to 100 mg, preferably 6.25 mg, 12.5 mg, 25 mg, 50 mg, 75 mg or 100 mg, of captopril; from about 2.5 mg to about 20 mg, preferably 2.5 mg, 5 mg, 10 mg or 20 mg, of enalapril; from about 10 mg to about 20 mg, preferably 10 mg or 20 mg, of fosinopril; from about 2.5 mg to about 4 mg, preferably 2 mg or 4 mg, of perindopril; from about 5 mg to about 20 mg, preferably 5 mg, 10 mg or 20 mg, of quinapril; or from about 1.25 mg to about 5 mg, preferably 1.25 mg, 2.5 mg, or 5 mg, of ramipril. Preferred is t.i.d. administration.

Especially preferred are low dose combinations.

The following examples illustrate the above-described invention; however, it is not intended to restrict the scope of this invention in any manner.

FORMULATION EXAMPLE 1

Film-Coated Tablets:

| Components | Composition Per Unit (mg) | Standards |
|---|---|---|
| Granulation | | |
| Valsartan [=active ingredient] | 80.00 | |
| Microcrystalline cellulose/ Avicel PH 102 | 54.00 | NF, Ph. Eur |

-continued

| Components | Composition Per Unit (mg) | Standards |
|---|---|---|
| Crospovidone | 20.00 | NF, Ph. Eur |
| Colloidal anhydrous silica/ colloidal silicon dioxide/Aerosil 200 | 0.75 | Ph. Eur/ NF |
| Magnesium stearate | 2.5 | NF, Ph. Eur |
| Blending | | |
| Colloidal anhydrous silica/ colloidal silicon dioxide/Aerosil 200 | 0.75 | Ph. Eur/ NF |
| Magnesium stearate | 2.00 | NF, Ph. Eur |
| Coating | | |
| Purified water *) | — | |
| DIOLACK pale red 00F34899 | 7.00 | |
| Total tablet mass | 167.00 | |

*) Removed during processing.

The film-coated tablet is manufactured e.g. as follows:

A mixture of valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a screening mill. The resulting mixture is again premixed in a diffusion mixer, compacted in a roller compacter and then sieve through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tablets are coated with a film by using Diolack pale red in a perforated pan.

FORMULATION EXAMPLE 2

Film-coated Tablets:

| Components | Composition Per Unit (mg) | Standards |
|---|---|---|
| Granulation | | |
| Valsartan [= active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ colloidal silicon dioxide/Aerosil 200 | 1.50 | Ph. Eur/ NF |
| Magnesium stearate | 5.00 | NF, Ph. Eur |
| Blending | | |
| Colloidal anhydrous silica/ colloidal silicon dioxide/Aerosil 200 | 1.50 | Ph. Eur/ NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

FORMULATION EXAMPLE 3

Film-Coated Tablets:

| Components | Composition Per Unit (mg) | Standards |
|---|---|---|
| Core Internal phase | | |
| Valsartan [=active ingredient] | 40.00 | |
| Silica, colloidal anhydrous (Colloidal silicon dioxide) [=Glidant] | 1.00 | Ph. Eur, USP/NF |
| Magnesium stearate [=Lubricant] | 2.00 | USP/NF |
| Crospovidone [Disintegrant] | 20.00 | Ph. Eur |
| Microcrystalline cellulose [=Binding agent] | 124.00 | USP/NF |
| External phase | | |
| Silica, colloidal anhydrous, (Colloidal silicon dioxide) [=Glidant] | 1.00 | Ph. Eur, USP/NF |
| Magnesium stearate [Lubricant] | 2.00 | USP/NF |
| Film Coating | | |
| Opadry ® brown OOF 16711*) | 9.40 | |
| Purified Water**) | — | |
| Total tablet mass | 199.44 | |

*)The composition of the Opadry ® brown OOF16711 coloring agent is tabulated below.
**)Removed during processing Opadry® Composition:

| Ingredient | Approximate % Composition |
|---|---|
| Iron oxide, black (C.I. No. 77499, E 172) | 0.50 |
| Iron oxide, brown (C.I. No. 77499, E 172 | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

FORMULATION EXAMPLE 4

Capsules:

| Components | Composition Per Unit (mg) |
|---|---|
| Valsartan [=active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |

| Components | Composition Per Unit (mg) |
|---|---|
| Titanium dioxide | 1.540 |
| Gelatin | 74.969 |
| Total tablet mass | 209.50 |

The tablet is manufactured e.g. as follows:

Granulation/Drying

Valsartan and micromystallin cellulose are spray-granulated in a fluidised bed granulator with a granulating solution consisting of povidone and sodium lauryl sulphate dissolved in purified water. The granulate obtained is dried in a fluidised bed dryer.

Milling/Blending

The dried granulate is milled together with crospovidone and magnesium stearate. The mass is then blended in a conical srew type mixer for approximately 10 minutes.

Encapsulation

The empty hard gelatin capsules are filled with the blended bulk granules under controlled temperature and humidity conditions. The filed capsules are dedustee, visually inspected, weightchecked and guarantied until by Quality assurance department.

FORMULATION EXAMPLE 5

Capsules:

| Components | Composition Per Unit (mg) |
|---|---|
| Valsartan [=active ingredient] | 160.00 |
| Microcrystalline cellulose | 50.20 |

| Components | Composition Per Unit (mg) |
|---|---|
| Crospovidone | 26.00 |
| Povidone | 25.00 |
| Magnesium stearate | 2.60 |
| Sodium lauryl sulphate | 1.20 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 342.00 |

The formulation is manufactured e.g. as described in Formulation Example 4.

FORMULATION EXAMPLE 6

Hard Gelatine Capsule:

| Components | Composition Per Unit (mg) |
|---|---|
| Valsartan [=active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

EXAMPLES 7 to 11

| | Example | | | | |
|---|---|---|---|---|---|
| | 7 | 8 | 9 | 10 | 11 |
| Components | Amount per Unit (mg) | Amount per Unit (mg) | Amount per Unit (mg) | Amount per Unit (mg) | Amount per Unit (mg) |
| Granulation | | | | | |
| Valsartan Drug Substance | 80.000 | 160.000 | 40.000 | 320.000 | 320.000 |
| Microcrystalline Cellulose (NF, Ph. Eur.)/Avicel PH 102 | 54.000 | 108.000 | 27.000 | 216.000 | 216.000 |
| Crospovidone (NF, Ph. Eur.) | 15.000 | 30.000 | 7.500 | 80.000 | 60.000 |
| Colloidal Anhydrous Silica (Ph. Eur.)/Colloidal Silicon Dioxide (NF)/Aerosil 200 | 1.500 | 3.000 | 0.750 | 3.000 | 6.000 |
| Magnesium Stearate (NF, Ph. Eur.) | 3.000 | 6.000 | 1.500 | 10.000 | 12.000 |
| Blending | | | | | |
| Colloidal Anhydrous Silica (Ph. Eur.)/Colloidal Silicon Dioxide (NF)/Aerosil 200 | — | — | — | 3.000 | — |
| Magnesium Stearate, NF, Ph. Eur. | 1.500 | 3.000 | 0.750 | 8.000 | 6.000 |
| Core Weight/mg | 155.000 | 310.000 | 77.500 | 640.000 | 620.000 |
| Coating | — | — | 3.800 | 15.000 | 16.000 |

EXAMPLE 12

Hard Gelatin Capsule:

| Component | Amount per unit [mg] |
|---|---|
| Capsule | |
| Fluvastatin Sodium [1] | 21.481 [2] |
| Calcium Carbonate | 62.840 |
| Sodium Bicarbonate | 2.000 |
| Microcrystalline Cellulose | 57.220 |
| Pregelatinized Starch | 41.900 |
| Purified Water [3] | Q.S. |
| Magnesium Stearate | 1.050 |
| Talc | 9.430 |
| Target Capsule Fill Weight | 195.92 |
| Capsule Shell | |
| Hard gelatin Capsule Shell | 48.500 |
| Branding Ink (pre-printed) | |
| White Ink | Trace |
| Red Ink | Trace |
| Target Capsule Weight | 244.42 |

[1] includes a 2% overage for moisture
[2] 20 mg of free acid is equivalent to 21.06 mg Na salt
[3] partially removed during processing

EXAMPLE 13

Hard Gelatin Capsule:

| Component | Amount per unit [mg] |
|---|---|
| Fluvastatin Sodium | 42.962 [1] [2] |
| Calcium Carbonate | 125.680 |
| Sodium Bicarbonate | 4.000 |
| Microcrystalline Cellulose | 114.440 |
| Pregelatinized Starch | 83.800 |
| Purified Water [3] | Q.S. |
| Magnesium Stearate | 2.100 |
| Talc | 18.860 |
| Target Capsule Fill Weight | 391.840 |
| Capsule Shell | |
| Hard gelatin Capsule Shell | 76.500 |
| Branding Ink (pre-printed) | |
| White Ink | Trace |
| Red Ink | Trace |
| Target Capsule Weight | 468.34 |

[1] includes a 2% overage for moisture
[2] 20 mg of free acid equivalent to 21.06 mg Na salt
[3] partially removed during processing

EXAMPLE 14

Round, Slightly Bi-Convex, Film-Coated Tablets with Beleved Edges:

| Component | Amount per unit [mg] |
|---|---|
| Table Core | |
| Fluvastatin Sodium [1] | 84.24 [2] |
| Cellulose Microcrystalline/Microcrystalline cellulose fine powder | 111.27 |
| Hypromellose/Hydroxypropyl methyl cellulose (Methocel K100LVP CR; HPMC100 cps) | 97.50 |
| Hydroxypropyl cellulose (Klucel HXF) | 16.25 |
| Potassium hydrogen carbonate/Potassium bicarbonate | 8.42 |
| Povidone | 4.88 |
| Magnesium stearate | 2.44 |
| Core Tablet Weight | 325.00 |
| Coating | |
| Coating premix - Opadry Yellow (00F22737) | 9.75 |
| Total Weight | 334.75 |
| Water, purified [3] | Q.S. |

[1] 84.24 mg of the sodium salt of fluvastatin is equivalent to 80 mg of fluvastatin free acid
[2] to be adjusted for moisture (LOD)
[3] removed during processing

EXAMPLE 15

Round, Biconvex, Beveled-Edged, Film-Coated Tablets:

| Component | Unit wt./Vol. [mg] | Unit wt./Vol. [mg] | Unit wt./Vol. [mg] | Unit wt./Vol. [mg] |
|---|---|---|---|---|
| Benazepril Hydrochloride | 5.00 | 10.00 | 20.00 | 40.00 |
| Lactose Monohydrate, NF | 142.00 | 132.00 | 117.00 | 97.00 |
| Pregelatinized Starch, NF | 8.00 | 8.00 | 8.00 | 8.00 |
| Colloidial Silicon Dioxide, NF (Cab-O-Sil, M-5) | 1.00 | 1.00 | 1.00 | 1.00 |
| Crospovidone, NF | 3.00 | 3.00 | 3.00 | 3.00 |
| Microcrystalline Cellulose, NF | 18.00 | 18.00 | 18.00 | 24.25 |
| Hydrogenated Castor Oil, NF | 8.00 | 8.00 | 8.00 | 1.75 |
| Magnesium Stearate, NF | | | | |
| Color: | | | | 0.50 |
| Yellow-Brown (suspension) | — | | 2.00 | |
| Red-Brown (suspension) | | | | 0.50 |
| Purified Water, USP | trace | trace | trace | trace |

-continued

| Component | Unit wt./Vol. [mg] | Unit wt./Vol. [mg] | Unit wt./Vol. [mg] | Unit wt./Vol. [mg] |
|---|---|---|---|---|
| Opadry Color: | | | | |
| Yellow | 8.38 | 8.38 | | |
| Pink | | | 8.38 | 8.38 |
| Total | 193.38 | 190.38 | 183.88 | 183.88 |

EXAMPLE 16

Film-Coated Tablets:

The following constituents are processed for the preparation of 10 000 tablets each containing 100 mg of active ingredient:

| | |
|---|---|
| hemi-fumarate of the compound of formula (1) | 1000 g |
| corn starch | 680 g |
| colloidal silicic acid | 200 g |
| magnesium stearate | 20 g |
| stearic acid | 50 g |
| sodium carboxymethyl starch | 250 g |
| water | quantum satis |

A mixture of one of the compounds of formula I mentioned in the preceding Examples as active ingredient, 50 g of corn starch and the colloidal silicic acid is processed into a moist mass with starch paste prepared from 250 g of corn starch and 2.2 kg of demineralised water. The mass is forced through a sieve having a mesh size of 3 mm and dried at 45° for 30 minutes in a fluidised bed drier. The dried granules are pressed through a sieve having a mesh size of 1 mm, mixed with a previously sieved mixture (1 mm sieve) of 330 g of corn starch, the magnesium stearate, the stearic acid and the sodium carboxymethyl starch, and compressed to form slightly biconvex tablets.

What is claimed is:

1. A pharmaceutical composition comprising the renin inhibitor of formula (I)

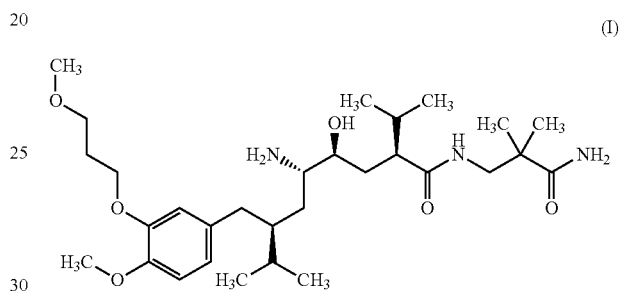

(I)

as a hemi-fumarate, hydrochlorothiazide and a carrier.

2. The composition according to claim 1 for the treatment of hypertension.

3. The composition according to claim 1 for simultaneous separate or sequential use.

* * * * *